United States Patent
Toftness

(10) Patent No.: US 7,438,074 B1
(45) Date of Patent: Oct. 21, 2008

(54) METHOD FOR ASSESSING THE CONDITION OF THE SPINE

(75) Inventor: David R. Toftness, Amery, WI (US)

(73) Assignee: Toftness Post Graduate School of Chiropractic, Inc., Amery, WI (US)

( * ) Notice: Subject to any disclaimer, the term of this patent is extended or adjusted under 35 U.S.C. 154(b) by 1008 days.

(21) Appl. No.: 10/347,840

(22) Filed: Jan. 17, 2003

Related U.S. Application Data

(63) Continuation-in-part of application No. 09/781,489, filed on Feb. 13, 2001, now abandoned.

(60) Provisional application No. 60/183,292, filed on Feb. 17, 2000.

(51) Int. Cl.
*A61B 19/00* (2006.01)

(52) U.S. Cl. ..................................... 128/898

(58) Field of Classification Search ................. 128/898
See application file for complete search history.

(56) References Cited

U.S. PATENT DOCUMENTS 4,479,498 A * 10/1984 Toftness ...................... 600/407

OTHER PUBLICATIONS

Walker Scientific "Fluxgate Magnetometers" Feb. 19, 1999, http://web.archive.org/web/19990219170515/http://www.walkers-scientific.com/Magnetometers/fluxgatemsgnetometer.html.*

Zhang et al. "The effect of low force chiropractic adjustments on body surface electromagnetic field" http://www.jcca-online.org/client/cca/JCCA.nsf/objects/V48-1-P29/$file/V48-1-P29.pdf.*

Hawkinson, E.J. et al., "Evaluation of the Toftness system of chiropractic adjusting for the relief of acute pain of musculo-skeletal origin" Chiropractic Techniques, vol. 4, No. 2, May 1992, pp. 57-60.

Snyder, B.J. & Sanders, G.E., "Evaluation of the Toftness system of chiropractic adjusting for subjects with chronic back pain, or chronic tension headaches or primary dysmenorrhea" Chiropractic Technique, vol. 8, No. 1, Feb. 1996, pp. 1-7.

Zhang, J. and Snyder, B.J., "The Effect of Low Force Chiropractic Adjustments on Body Surface Electromagnetic Field" Logan College of Chiropractic, Chester-field, MO 63006, Oct. 30, 2000.

* cited by examiner

*Primary Examiner*—Thomas J Sweet
(74) *Attorney, Agent, or Firm*—Tipton L. Randall

(57) ABSTRACT

A method of assessing the spine of a patient is provided, the method comprising (a) placing a patient to be assessed in a prone position; (b) providing a magnetometer; (c) identifying a vertebra of the spine to be assessed; (d) placing the magnetometer over the vertebra to be assessed and obtaining a magnetometer reading of the vertebra; (e) identifying at least one additional vertebra to be assessed and repeating step (d) for the at least one additional vertebra. The method also includes delivering a chiropractic adjustment to the vertebra and obtaining another magnetometer reading to determine if a change of about 1.0% absolute value has occurred.

12 Claims, 5 Drawing Sheets

METHOD FOR ASSESSING THE CONDITION OF THE SPINE

CROSS REFERENCE TO RELATED APPLICATION

This application is a continuation in part of U.S. patent application Ser. No. 09/781,489, filed 13 Feb. 2001, now abandoned, which is hereby incorporated by reference. This application also claims the benefit under 35 U.S.C. § 119(e) of provisional application Ser. No. 60/183,292, filed 17 Feb. 2000. Application Ser. No. 60/183,292 is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

FIELD OF THE INVENTION

The present invention relates to a method of assessing and treating the spine of a patient, and more particularly, to a method of assessing and treating the spine of a patient employing a magnetometer.

BACKGROUND OF THE INVENTION

Over 100 years ago, it was discovered that vertebrae in the spine that are displaced slightly can cause neck pain, low back pain, headaches and a whole host of internal conditions including, but not limited to, dysmenorrhea, colitis, and otitis media. The term subluxation is commonly used in chiropractic to indicate such vertebrae displacement. Chiropractic is concerned with preservation and restoration of health and focuses particular attention on the subluxation. Throughout the present disclosure, the term subluxation shall mean a complex of functional and/or structural and/or pathological articular changes that compromise neural integrity and may influence organ system function and general health, the definition provided by the American Chiropractic Association. A subluxation is evaluated, diagnosed and managed through the use of chiropractic procedures based on the best available rationale and empirical evidence. Since the discovery of subluxation, practitioners have been trying to find better ways to locate and correct spinal subluxations. To date, many methods have been used. These include palpation of the spine to feel physical displacement, x-ray of the spine to observe the physical displacement, and infrared and millimeter wave thermography of the spine to locate the displacement by the interference that it causes on the nervous system.

The methods used to date to locate spinal subluxations have disadvantages. For example, palpation of the spine requires that the practitioner be highly trained, and the inter-examiner reliability has been shown to be only moderately reliable. X-rays have a certain amount of danger associated with them and the image is only a snapshot in time. Infrared and millimeter wave thermography are associated with instrument errors and environmental errors that makes the use of them less than perfect. It would be beneficial to humanity if these disadvantages could be overcome.

Currently, there is a need of a method for assessing the condition the spine that is repeatable, sensitive and non-invasive, with an instrument that is portable and provides immediate information regarding the status of the spine. There is a need of a method for assessing the condition the spine that does not carry with it the disadvantages noted herein above.

SUMMARY OF THE INVENTION

The present invention provides a method for assessing the condition the spine that is repeatable, sensitive and non-invasive. The present invention provides a method for assessing the condition the spine with an instrument that is portable and provides immediate information regarding the status of the spine. The present invention provides a method for characterizing and assessing the condition of spinal health using an electromagnetic or magnetic device. The method of the present invention is contemplated as being applicable to body areas other than the spine, as well.

In the broadest scope of the invention, a method is provided for assessing the condition of a musculoskeletal structure of a mammal. The method comprises the steps of providing a hand-held magnetometer, and detecting values of magnetic field along the musculoskeletal structure of the mammal. In a further embodiment of the invention, the method for assessing the condition of a musculoskeletal structure of a mammal includes the steps of providing a hand-held magnetometer, and detecting values of magnetic field along the musculoskeletal structure of the mammal before and after chiropractic adjustment thereto. In a preferred embodiment, the musculoskeletal structure is the spinal column and the mammal is a human.

In a more specific embodiment of the invention, a method is provided for assessing the condition of a spinal column of a human. The method comprising the steps of placing a human to be assessed in a prone position; providing a hand-held magnetometer; placing the magnetometer over a selected vertebra of the spinal column of the human; determining an initial magnetic field value for the selected vertebra; performing a chiropractic adjustment to the spinal column; redetermining a magnetic field value for the selected vertebra; and assessing if the selected vertebra shows changes from the chiropractic adjustment by determining if the change in magnetic field value is greater than an absolute value of about 1.0% of the initial magnetic field value for the selected vertebra.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION OF THE INVENTION

The present invention is believed to be applicable to a variety of different human body areas, and has been found to be particularly suited for assessing subluxated vertebra of the spine, as well as determining when treatment has restored the vertebra to a normal condition, that is, without subluxation. The term "without subluxation" is commonly used in chiropracty to indicate a normal condition for the vertebrae. Throughout the present disclosure, the term "without subluxation" shall mean a normal condition for the vertebrae, that is, without a complex of functional and/or structural and/or pathological articular changes that compromise neural integrity and may influence organ system function and general health, the definition provided by the American Chiropractic Association. While the present invention is not necessarily limited to assessment and treatment of the vertebra of the spine, various aspects of the invention may be appreciated through a discussion of various examples using this context.

According to an example embodiment of the present invention, a method of assessing the condition a body area, such as the spine, of a patient is provided. The method includes placing a patient to be diagnosed in a prone position. A magnetometer is provided, and an initial body area, such as a vertebra of the spine, to be assessed is identified. The magnetometer is placed over the initial body area, such as a vertebra, to be assessed and an initial magnetometer magnetic field value is measured for the initial body area, such as a vertebra. A chiropractic adjustment is then made to the initial body area, such as a vertebra of the spine, then a magnetometer magnetic field value is again measured for the initial body area, such as a vertebra. It is then assessed if the initial body area, such as a vertebra, shows changes from the chiropractic adjustment by determining if the change in magnetic field value is greater than an absolute value of about 1.0% of the initial magnetic field value for the initial body area, such as a vertebra.

Figure 1:
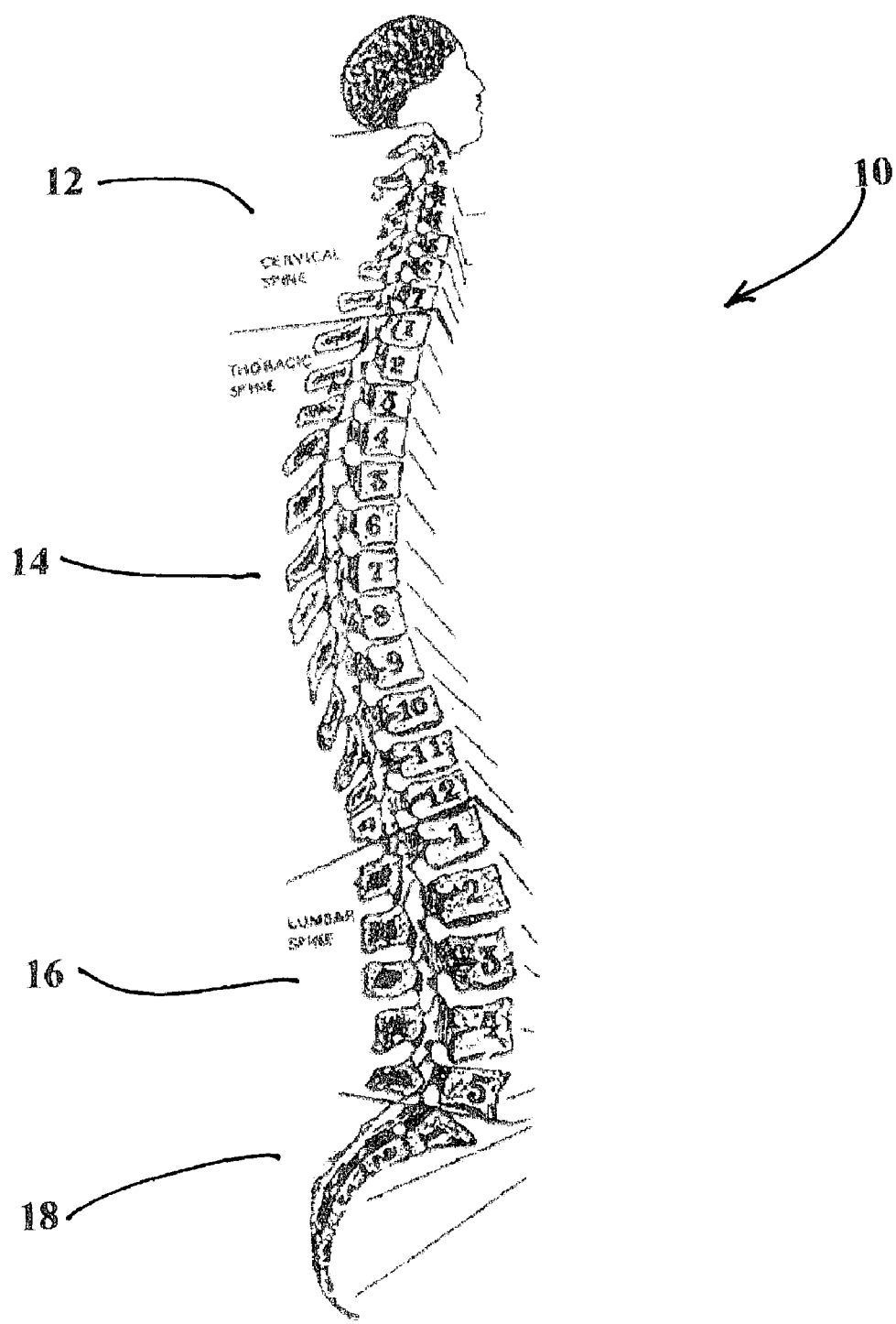
FIG. 1 is a conceptual side view of a human spine.

Referring to FIG. 1, a human spine is shown. The human spine 10 has twenty six vertebrae, which are divided into four regions. These regions are the cervical region 12 which has seven vertebrae, the thoracic region 14 which has twelve vertebrae, the lumbar region 16 which has five vertebrae and the sacrum region 18 which has two vertebrae.

When spinal vertebra in a human are out of alignment, the nervous system is disturbed and symptoms and/or disease ensue. When vertebra are replaced to their normal juxtaposition, the nervous system interference is reduced and health returns. The nervous system is electrical in nature and exhibits known electrical properties including, but not limited to, conduction, EMF fields and the like.

The earth has a magnetic field of its own. Extensive mapping of this magnetic field has been achieved employing magnetometers. The magnetic field is commonly measured along the X, Y and Z axis of the Cartesian coordinate system. Each of the three components (X, Y, Z) has a different magnitude, and the magnitude of each component varies from location to location. The vertical magnetic component (Z axis) varies in the range of about 36,000 to about 54,000 nanoTesla (nT) or about 360 to about 540 milliGauss (mG) within the United States.

The method of the present invention is based on the Applicant's discovery that the human spine emits a magnetic field that is superimposed upon the earth's magnetic field, and that subluxated spinal vertebrae superimpose a magnetic field of greater magnitude than do normal (without subluxation) vertebrae. By measuring the magnetic field vertical or Z axis component of the spine of a patient in the prone position, the condition of the spinal vertebrae can be assessed. It has been discovered that an improvement in the condition of vertebrae of the human spine is indicated by a change in the measured magnetic field vertical or Z-axis component of a prone human. Improvement includes, but is not limited to, reduced pain, improved movement, etc. A measured absolute value change in the magnetic field vertical or Z-axis component of about 1.0% following chiropractic adjustment correlates with improved condition of the vertebrae. As mentioned above, the magnetic field of the human, spine is superimposed upon the earth's magnetic field, so variations in the magnitude of the measured value occur, depending upon location of the individual on the earth's surface. Thus, a magnitude change is important and not just the total magnitude measured.

One instrument that has been discovered as being capable of use for obtaining magnetic measurements of the spine is the Walker Scientific Fluxgate Magnetometer. The method of the present invention, however, is intended to encompass the use of any instrument which measures electromagnetic or magnetic force or any magnetometer. Although the present invention is not intended to be limited thereby, information regarding Walker Scientific's Fluxgate Magnetometers is available from Walker Scientific, located on Rockdale Street, Worcester, Mass., 01606. Examples of Walker Scientific Fluxgate Magnetometers which may be utilized in the method of the present invention are the FGM-4DTAM Triaxial Magnetometer, the FGM-5DTAA Triaxial Magnetometer, the FGM-3D2L Single Axis Fluxgate Magnetometer, the FGM-3D2T Single Axis Fluxgate Magnetometer, the FGM-4D2L Single Axis Fluxgate Magnetometer, the FGM-4D2T Single Axis Fluxgate Magnetometer, the FGM-3D2LN Single Axis Fluxgate Magnetometer, the FGM-3D21N Single Axis Fluxgate Magnetometer, the FGM-4D2LN Single Axis Fluxgate Magnetometer and the FGM-4D2TN Single Axis Fluxgate Magnetometer. The measurement is taken with the Walker Scientific Fluxgate Magnetometer from above the patient, using the vertical or Z axis of the magnetometer probe. The single axis probe is positioned above the prone patient's spine with the single probe axis oriented vertically downward. Alternatively, the triaxial probe is also positioned above the prone patient's spine with the triaxial probe Z axis oriented vertically downward.

In one embodiment of the method of the present invention, the patient is placed in a prone position. The Fluxgate magnetometer probe is placed successively over each vertebra of the spine that the practitioner selects for assessment, and a magnetometer reading value is obtained for each. The vertebra of the spine that has the highest reading value is assessed as a subluxated vertebra. A chiropractic adjustment is delivered to the subluxated vertebra that has the highest reading. The chiropractic adjustment may be made according to any chiropractic adjustment system. For example, an adjustment may be made using the Toftness System, described in the articles "Evaluation of the Toftness System of Chiropractic Adjusting for the Relief of Acute Pain of Musculoskeletal Origin" and "Evaluation of the Toftness System of Chiropractic Adjusting for Subjects with Chronic Back Pain, or Chronic Tension Headaches or Primary Dysmenorrhea", published in Chiropractic Technique in May, 1992, and February, 1996, respectively.

A magnetometer reading is again taken of the vertebra or vertebral area following the chiropractic adjustment. A chiropractic adjustment to the spine is complete and successful when the reading value over the vertebra displays an absolute magnitude change of about 1.0%. This method may alternatively be performed on the vertebral regions of the spine. For example, one magnetometer reading value is taken of the cervical area, a chiropractic adjustment is made to the cervical area and a second magnetometer reading value is taken of the cervical area following the chiropractic adjustment. This process is repeated for each of the remaining three vertebral regions. FIGS. 2-5 are flow chart diagrams of the several embodiments of the method of the present invention.

Figure 2:
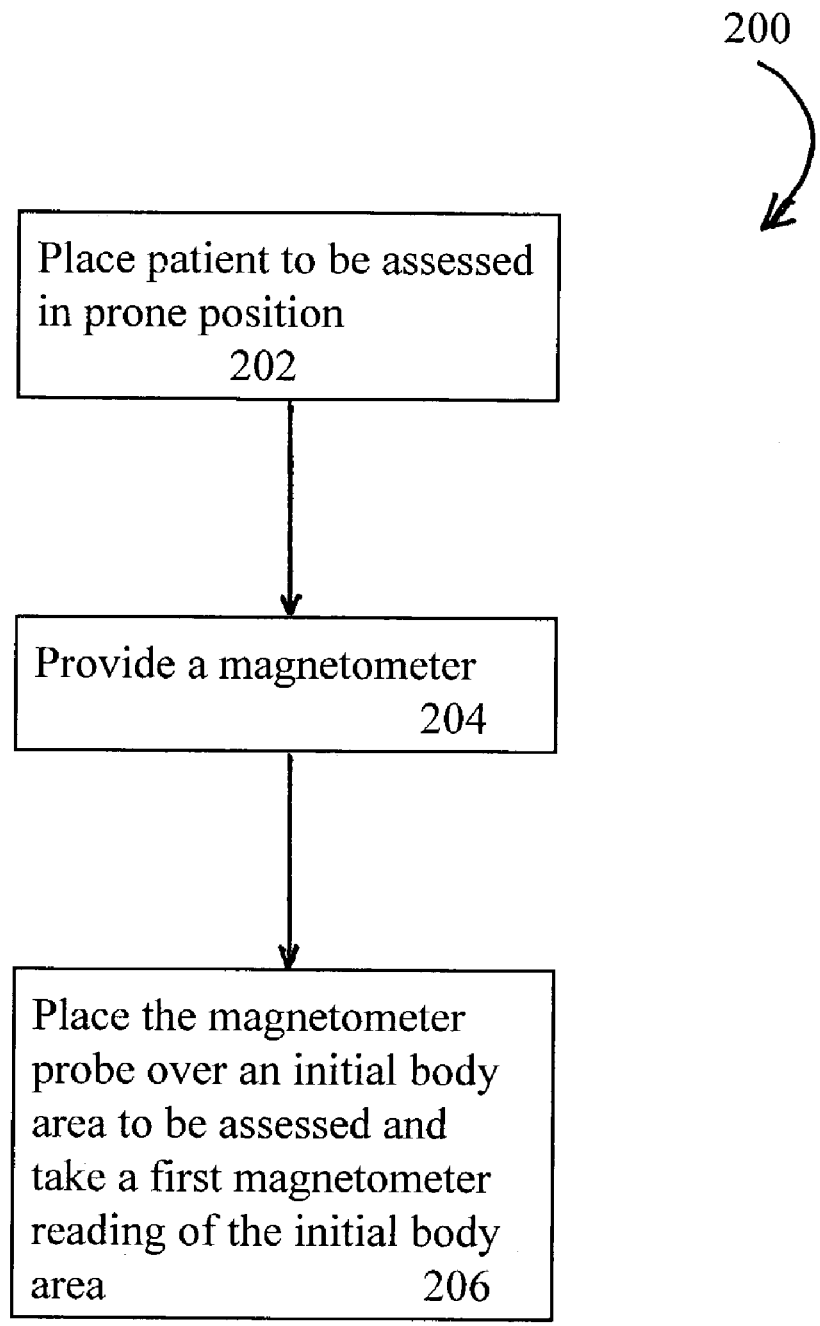
FIG. 2 is a flow chart of one method of the present invention.

Referring to FIG. 2, the method 200 is shown. A patient to be assessed is placed in a prone position (202). A magnetometer is provided (204). The magnetometer probe is placed over an initial body area to be diagnosed and a first magnetometer reading of the initial body area is taken (206) along the Z-axis which is oriented vertically downward.

Figure 3:
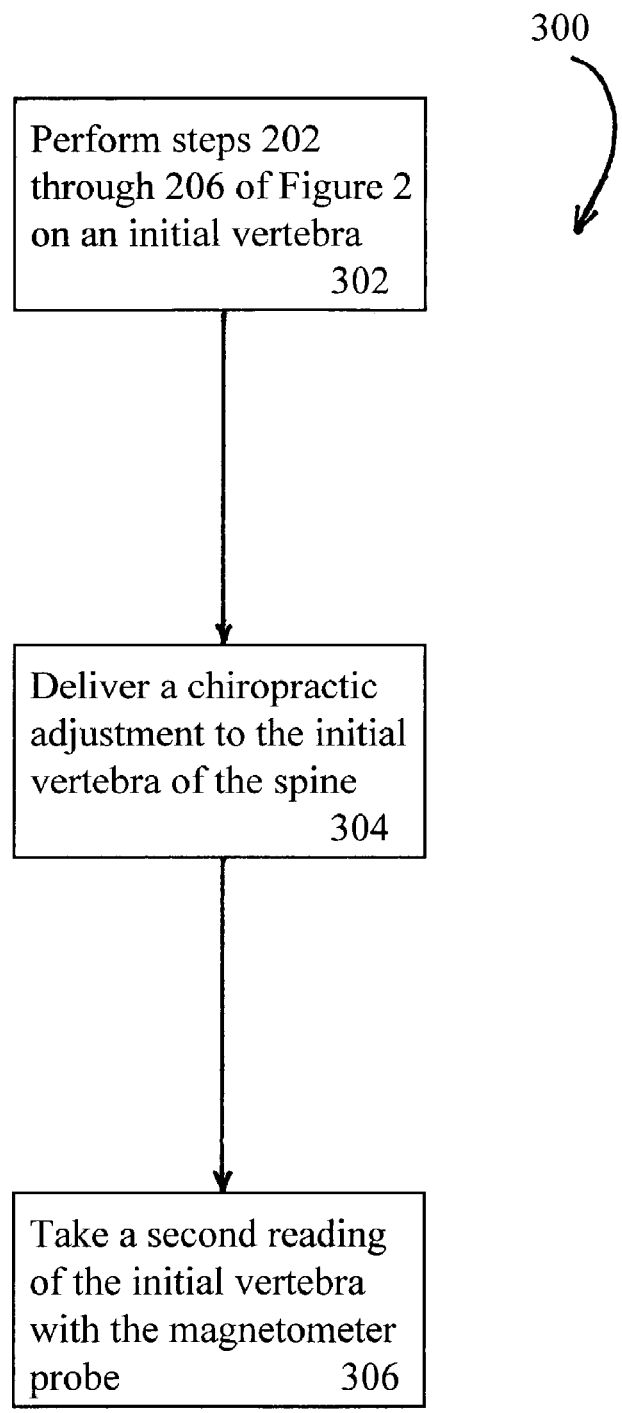
FIG. 3 is a flow chart of another method of the present invention.

Referring to FIG. 3, method 300 is shown. Steps 202-206 of FIG. 2 are repeated where the initial body area is an initial vertebra of the spine (302). A chiropractic adjustment is delivered to the initial vertebra (304). A second magnetometer reading is taken of the initial vertebra with the magnetometer (306) to determine whether the magnetometer reading of initial vertebra has changed by an absolute value of about 1.0%. A magnetometer reading value in the range of about 420 mG is normally obtained, although this value can vary, depending on the particular location of the patient on the earth's surface.

Figure 4:
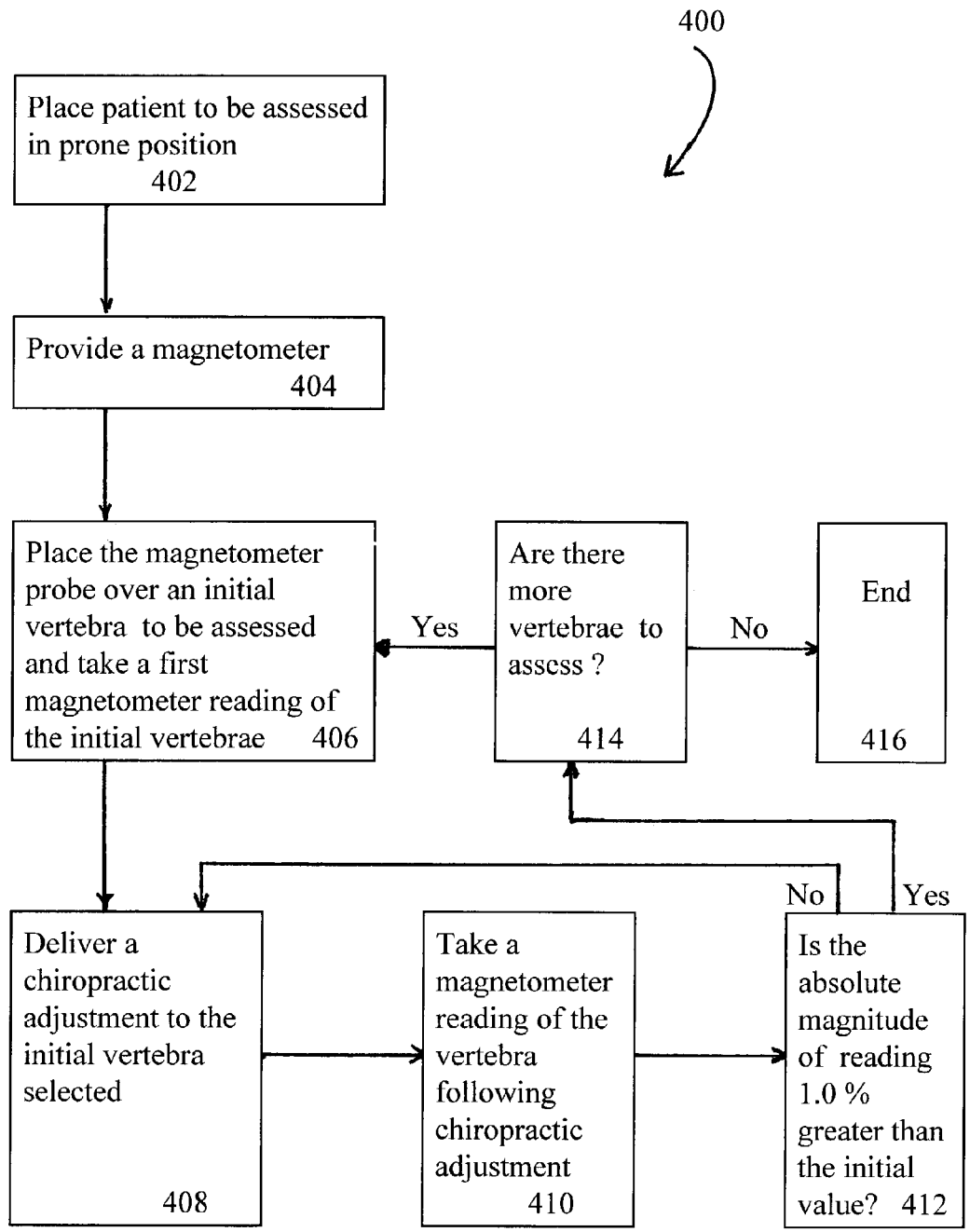
FIG. 4 is a flow chart of another method of the present invention.

Referring now to FIG. 4, method 400 is shown. The patient to be assessed is placed in a prone position (402). A magnetometer, such as a Walker Scientific Fluxgate Magnetometer, is provided (404). The magnetometer probe is placed over a vertebra to be assessed and a first magnetometer reading is taken (406). A chiropractic adjustment is then delivered to the vertebra (408). A magnetometer reading is taken (410) following the adjustment. If the reading value has changed more than about 1.0% in absolute magnitude for vertebra, the process is complete for that vertebra (412). If not, a further chiropractic adjustment to the vertebra may be made and a subsequent magnetometer reading taken until the reading value the reading value has changed more than about 1.0% in absolute value. The process continues until there are no more vertebrae to assess and treat (416). A magnetometer reading value in the range of about 420 mG is normally obtained, although this value can vary, depending on the particular location of the patient on the earth's surface.

Figure 5:
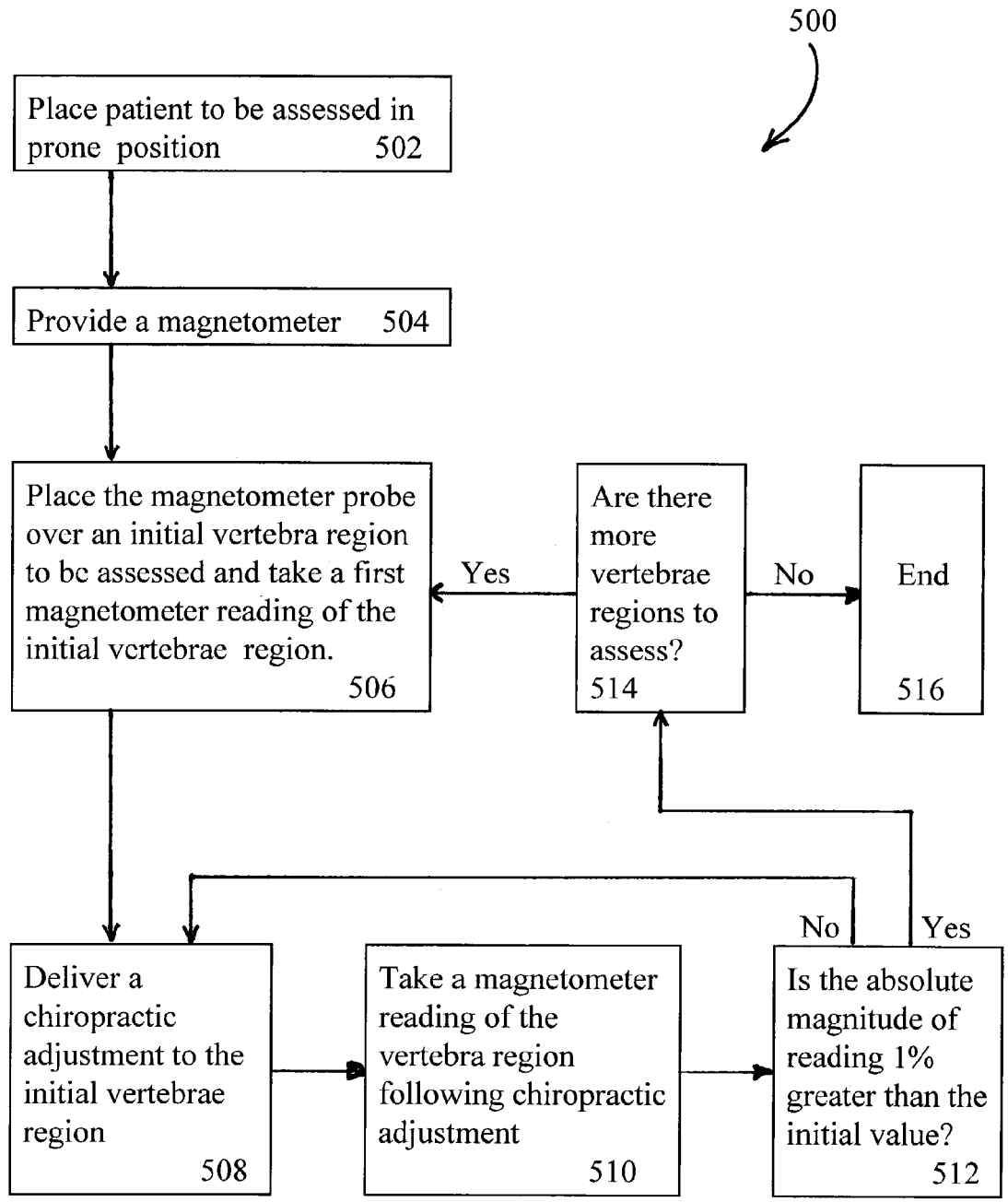
FIG. 5 is a flow chart of another method of the present invention.

The methods set forth in FIGS. 2-4 are suitable for assessment and treatment of body areas such as spinal regions. Referring now to FIG. 5, following the steps (502) and (504), the initial magnetometer reading (506) is performed on a vertebral region instead of a single vertebra. A chiropractic adjustment to the vertebral region is made (508). A follow up magnetometer reading is taken (510) to determine if the reading value has changed more than about 1.0% in absolute value for the vertebral region (506). This process is then repeated for each of the three remaining vertebral regions (514) until there are no more vertebral regions (516). Again, a magnetometer reading value in the range of about 420 mG is normally obtained, although this value can vary, depending on the particular location of the patient on the earth's surface.

EXAMPLE

Method: Forty-four randomly selected subjects were assigned into control (20 subjects) and experimental groups (24 subjects) in a pre- and post-test design. Subjects in the control group received no chiropractic adjustment. A Triaxial Fluxgate Magnetometer FGM-5DTAA (Walker Scientific, Worcester, Mass.) with five digit display and resolution of 1 nT in a 100,000 nT field was used for magnetic field detection. Thus, small variations in magnetic field can be measured in the presence of a large field, such as the earth's magnetic field. The magnetic field components can be displayed in nanotesla (nT), microtesla (mT) or milligauss (mG). The FGM-5DTAA instrument has a sample rate of 69 samples per second for real time magnetic field measurement. The instrument was calibrated according to the industrial standards for accurate magnetic field readings.

The magnetic field in the research room and on the adjustment table was monitored and recorded. The room magnetic field was measured in three dimensions, namely the X, Y and Z axes. While holding the instrument probe horizontally during testing, the X axis is detecting the magnetic field component from the south, the Y axis is detecting magnetic field component from the east, and the Z axis is detecting the magnetic component field from the ground (earth field). The room magnetic field was 416.11 mG at the Z axis, 137.61 mG at the X axis and 74.38 mG at the Y axis. The plain wood table had magnetic field readings in the range of 410.00 mG at the Z axis. A motorized Hi-Lo table had much higher magnetic field readings of 730.00 mG at the Z axis near the lumbar and sacral regions. Only the plain wood table was used in the study for magnetic measurements and for chiropractic adjustment. The magnetic field on the table with and without the subject and at different times was recorded. The magnetic field components did not change significantly over time with the subjects lying on this table.

The subjects' body surface (cervical, thoracic, lumbar and sacral areas) magnetic field Z axis component was determined in the prone position before and after the chiropractic adjustment. Magnetic field strength along the Z axis at the cervical, thoracic, lumbar and sacral areas were measured before the chiropractic adjustment at 5, 10 and 15 minutes of lying on the table. The average Z axis magnetic field reading from the 24 subjects in the experimental group was 424.61 mG at the cervical area, 423.83 mG at the thoracic area, 433.16 mG at the lumbar area, and 434.40 mG at the sacral area prior to chiropractic adjustment. A low force Toftness chiropractic adjustment was applied to the cervical, thoracic, lumbar and sacral areas as determined by the practitioner.

Results: The 24 subjects in the experimental group showed a significant decrease in Z axis magnetic field (mean ±SD in mG) after Toftness chiropractic adjustment at the cervical region from 424.49±9.07 mG to 416.43±11.65 mG ($p<<0.01$) and at the sacral regions from 432.06±7.60 mG to 427.13±5.52 mG ($p<0.01$). The Z axis magnetic field at the lumbar region decreased from 429.73±7.67 mG to 428.22±9.39 ($p>0.05$) and the Z axis magnetic field decreased at the thoracic region from 424.59±7.44 mG to 422.25±9.81 mG ($p>0.05$), but did not reach a statistically significant level for these two spinal regions. The average decrease of the Z axis magnetic field in the cervical region and in the sacral region was 8.06 mG and 4.93 mG.

In the control group, Z axis magnetic field readings were taken in the same fashion as in the experimental group but there were no significant Z axis magnetic field changes in all four spinal locations.

Referring to TABLE 1, data taken in the example using the method disclosed herein are presented where n equals the number of subjects (persons) observed. According to the method, a chiropractic adjustment to the spine is complete and successful when the magnetometer reading value over the vertebra shows an absolute change of about 1.0% following chiropractic adjustment. The p value of less than 0.05 is statistically significant and is another indicia of successful treatment.

TABLE 1

Magnetometer Measurements Before and After Chiropractic Adjustment

|  | n | MEAN (mG) | SD (mG) | P |
| --- | --- | --- | --- | --- |
| Cervical (before) | 24 | 424.49 | 9.07 | 0.00091 |
| Cervical (after) | 24 | 416.43 | 11.65 |  |
| Thoracic (before) | 24 | 424.59 | 7.44 | 0.113 |
| Thoracic (after) | 24 | 422.25 | 9.81 |  |
| Lumbar (before) | 24 | 429.73 | 7.67 | 0.348 |
| Lumbar (after) | 24 | 428.22 | 9.39 |  |
| Sacrum (before) | 24 | 432.06 | 7.60 | 0.00445 |
| Sacrum (after) | 24 | 427.13 | 5.52 |  |

The method of the present invention eliminates the dangers and disadvantages of prior methods of locating spinal subluxations. The method eliminates the unreliability of palpation as an assessment tool, the danger of x-rays, the necessity for a magnetically shielded room, and instrumental and environmental error associated with infrared and millimeter wave thermography. The use of a magnetometer and the Fluxgate Magnetometer in particular provides a method of assessment and treatment of spinal subluxation that is repeatable, reliable, sensitive, non-invasive, and portable, while providing immediate information on the status of the spine.

The invention has been described with reference to various specific and preferred embodiments and techniques. However, it should be understood that many variations and modifications may be made while remaining within the spirit and scope of the invention.

What is claimed is:

1. A method for assessing the condition of a musculoskeletal structure of a mammal, the method comprising the steps;
   (a) providing a hand-held magnetometer; and
   (b) detecting values of magnetic field along the musculoskeletal structure of the mammal.

2. The method for assessing the condition of a musculoskeletal structure of a mammal of claim 1, wherein the musculoskeletal structure of a mammal is a spinal column.

3. The method for assessing the condition of a musculoskeletal structure of a mammal of claim 1, wherein the mammal is a human.

4. The method for assessing the condition of a musculoskeletal structure of a mammal of claim 1, wherein the musculoskeletal structure is a spinal column and the mammal is a human.

5. A method for assessing the condition of a musculoskeletal structure of a mammal, the method comprising the steps;
   (a) providing a hand-held magnetometer; and
   (b) detecting values of magnetic field along the musculoskeletal structure of the mammal before and after chiropractic adjustment thereto.

6. The method for assessing the condition of a musculoskeletal structure of a mammal of claim 5, wherein the musculoskeletal structure of a mammal is a spinal column.

7. The method for assessing the condition of a musculoskeletal structure of a mammal of claim 5, wherein the mammal is a human.

8. The method for assessing the condition of a musculoskeletal structure of a mammal of claim 5, wherein the musculoskeletal structure is a spinal column and the mammal is a human.

9. The method for assessing the condition of a musculoskeletal structure of a mammal of claim 5, wherein the chiropractic adjustment is made to the musculoskeletal structure of the mammal at a point having the magnetic field value of greatest magnitude.

10. A method for assessing the condition of a spinal column of a human, the method comprising the steps;
    (a) placing a human to be assessed in a prone position;
    (b) providing a hand-held magnetometer;
    (c) placing the magnetometer over a selected vertebra of the spinal column of the human;
    (d) determining an initial magnetic field value for the selected vertebra;
    (e) performing a chiropractic adjustment to the spinal column;
    (f) redetermining a magnetic field value for the selected vertebra; and
    (g) assessing if the selected vertebra shows changes from the chiropractic adjustment by determining if the change in magnetic field value is greater than an absolute value of about 1.0% of the initial magnetic field value for the selected vertebra.

11. The method for assessing the condition of a spine of a human according to claim 10, wherein the hand-held magnetometer is a Fluxgate Magnetometer and the Z-axis of the magnetometer is oriented perpendicular to the spinal column of a human in the prone position.

12. The method for assessing the condition of a spine of a human according to claim 10, wherein the vertebra of the spinal column of the human selected has the magnetic field value of greatest magnitude.

* * * * *